United States Patent [19]

Brychta et al.

[11] Patent Number: 4,681,100

[45] Date of Patent: Jul. 21, 1987

[54] MULTINOZZLE GENERATOR FOR HIGH FREQUENCY NOZZLE VENTILATION OF LUNGS

[75] Inventors: Ondrej Brychta, Trencin; Vladimir Zabrodsky, Prague, both of Czechoslovakia

[73] Assignee: Konstruktiva Trencin, narodny podnik, Trencin, Czechoslovakia

[21] Appl. No.: 814,643

[22] Filed: Dec. 30, 1985

[30] Foreign Application Priority Data

Dec. 28, 1984 [CS] Czechoslovakia .................. 10492-84

[51] Int. Cl.⁴ ............................................ A61M 16/00
[52] U.S. Cl. ........................... 128/204.25; 128/207.14; 128/205.23; 137/602
[58] Field of Search ........................ 128/204.25, 203.11, 128/205.11, 911, 205.23; 604/83, 149; 417/178, 179, 180, 197; 137/602, 888, 889, 892, 897, 606

[56] References Cited

U.S. PATENT DOCUMENTS

| 282,074 | 7/1883 | Grimm | 417/180 |
| 4,425,914 | 1/1984 | Ray et al. | 128/203.12 |
| 4,537,188 | 8/1985 | Phuc | 128/204.25 |
| 4,543,951 | 10/1985 | Phuc | 128/911 |
| 4,596,247 | 6/1986 | Whitwam et al. | 128/204.25 |

FOREIGN PATENT DOCUMENTS 948476 8/1956 Fed. Rep. of Germany ...... 417/179

Primary Examiner—Henry J. Recla

[57] ABSTRACT

A multinozzle generator for high frequency ventilation of lungs reducing the danger of damages to lungs due to ventilation overpressure and enabling a ventilation of patients without limitation of age. The generator can be adapted to different throughflow characteristics and elastic resistance of the lungs. The generator is suitable for cleaning of air passages of the patient without interruption of the ventilation; it can perform selective ventilation of lungs by means of two generators using different overpressure and a simple generation of a final expiration overpressure.

9 Claims, 5 Drawing Figures

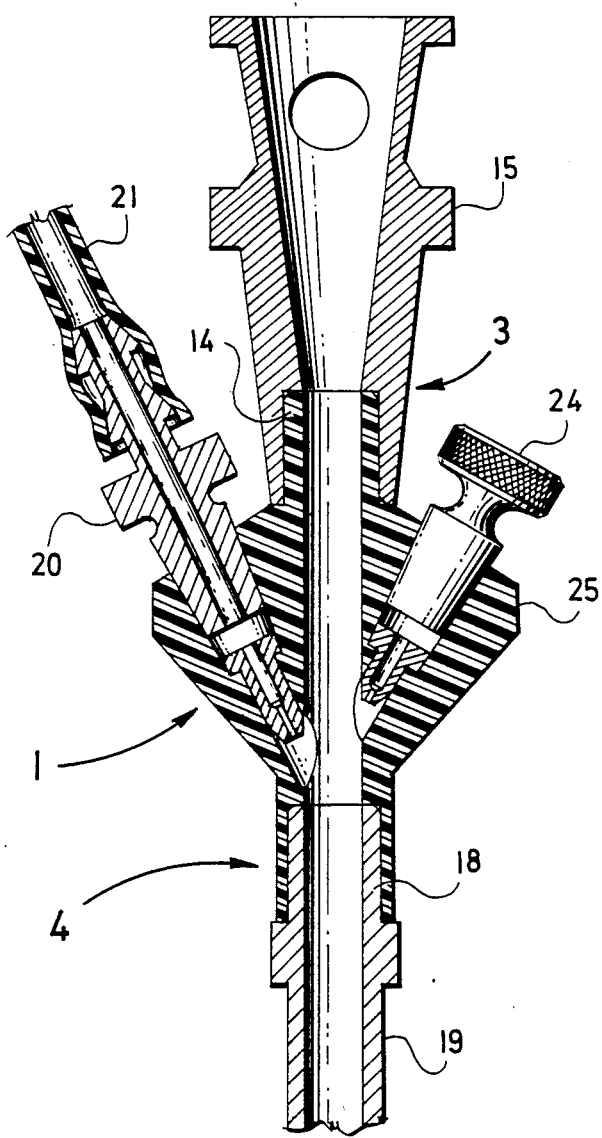
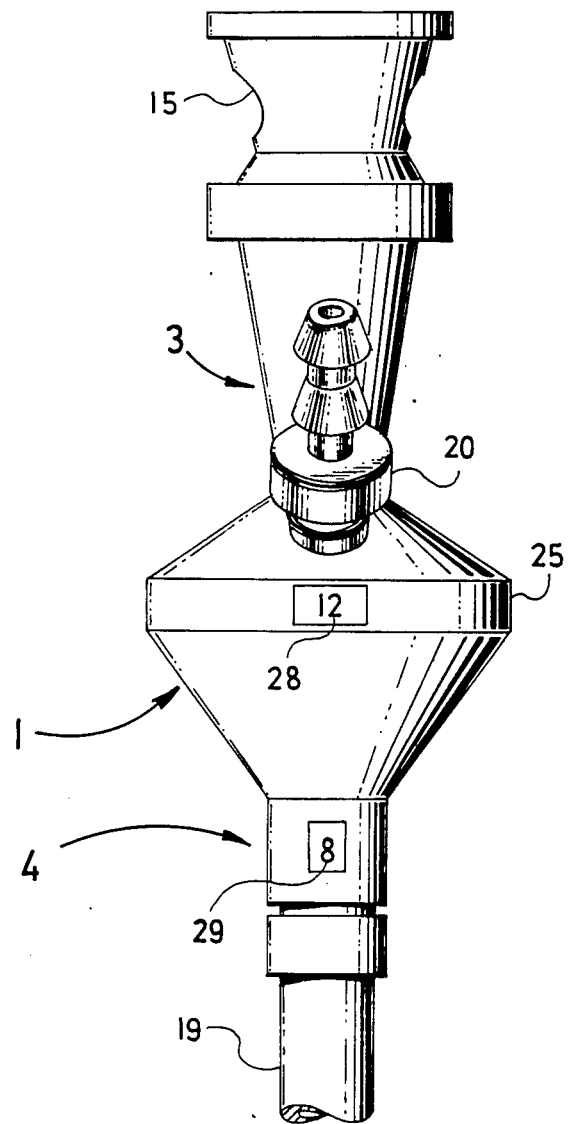
Fig. 3
Fig. 4

MULTINOZZLE GENERATOR FOR HIGH FREQUENCY NOZZLE VENTILATION OF LUNGS

BACKGROUND OF THE INVENTION

The invention relates to a multinozzle generator for high frequency ventilation of lungs.

The state of the art generator for high frequency nozzle ventilation of lungs comprises a nozzle of a certain nominal internal diameter having the shape of a relatively long tube which engages by its distal end into a cylindrical hollow of an extension of an intubation tube, the nominal internal diameter of which is equal to the nominal internal diameter of the tube. The tube forming the nozzle is situated in the axis of a cylindrical hollow of the extension and is usually fastened in a fitting of a humidifying supply means of gases and the extension of the intubation tube is by its cone inserted into the hollow of the fitting.

These known solutions of similar generators have a number of drawbacks.

In case a nominal internal diameter of the generator nozzle and a different internal diameter of the cylindrical hollow of the extension of the intubation tube are used, a different maximum generator overpressure and a different internal generator resistance are experienced even in case of a uniform insufflation pressure in the nozzle. For instance for a uniform internal diameter of the nozzle in case of a change to a double of the nominal diameter of the cylindrical hollow of the extension an approximately four times change of the maximum generator overpressure and an approximately eight times change of the internal resistance of the generator are obtained. This physical fact makes the programming of high frequency nozzle ventilation difficult and can also cause damages of lungs due to excessive overpressure.

Another drawback of known solutions is the difficulty of an adjustment of the generator to the instantaneous condition of lungs. For instance in case of a supporting nozzle ventilation, where this ventilation is superposed to the breathing activity of the patient, the maximum generator overpressure and the internal generator resistance have to be reduced and the superposed ventilation has to be adjusted to the breathing activity of the patient while maintaining a certain level of the insufflation pressure in the nozzle which induces the dynamic overpressure in the intubation tube. In case the air passages of the patient have a relatively high throughflow resistance, it is necessary to increase the maximum overpressure power of the generator and also to increase its internal resistance, which can only be achieved solely by a substantial increase of the insufflation overpressure, whereby the internal resistance of the generator increases only by about its square root.

A further drawback of known solutions of generators having a nozzle of the shape of a relatively long tube disposed along the axis of a cylindrical hollow or an extension of the intubation tube resides in the limitation of movement of the suction catheter in case the suction of the patient has to be performed without interruption of the ventilation, whereby this possibility of sucking without interruption of the ventilation is one of the advantages of high frequency nozzle ventilation. This advantage is also present in case the state of the art devices are used in connection with a bronchoscope, where the nozzle of the shape of a tube situated within the bronchoscope tube obstructs the optical tubus or an operational tool respectively.

Another drawback in the application of a nozzle of the shape of a relatively long tube resides in the substantial loss of power due to streaming of gases in a long narrowed passage.

SUMMARY OF THE INVENTION

It is an object of this invention to eliminate or at least to substantially mitigate the afore-mentioned drawbacks and to provide a multinozzle generator for high frequency nozzle ventilation which reduces the danger of damage to the lungs of the patient due to ventilation overpressure, which would allow the application of the apparatus to patients of different age and different throughflow resistance of lungs and which is capable to performing the sucking-off of air passages of the patient without interruption of the ventilation.

The multinozzle generator for high frequency nozzle ventilation according to this invention comprises a connection element disposed between devices used for treatment of lungs and between a tube which is introduced into air passages of the patient, said connecting element comprising a body with a cylindrical opening with a nominal internal diameter. The connecting element is further provided on one end with an upper throughflow connection and on the other end with a lower throughflow connection, whereby at least two inlet openings are provided in the body of said connecting element, in which opening nozzles are arranged, the nozzle outlets of which have different nominal internal diameters and are terminating into said cylindrical bore of the connecting element; the axis of the nozzle outlets form with the axis of the cylindrical bore an angle of 10 to 30 angular degrees; said connecting element can form a set with stepped internal diameters of nozzle outlets and different nominal internal diameters of nozzle outlets for each connecting element of the same ratio with the nominal diameter of the cylindrical bore.

The upper throughflow connection forms a cone for mounting in a fitting of a humidifying circuit or an upper stable connection for connection of the head of a bronchoscope and the lower throughflow connection forms a prolonged cone for the intubation tube or for a lower stable connection of a bronchoscope tube, whereby the nominal internal diameter of the cylindrical bore is equal to the nominal internal diameter of the intubation tube or of the bronchoscope tube.

The feeding openings form a standard conical connection for an insufflation connector of a catheter with an intermittent overpressure or for a connector of a catheter with a constant overpressure or also for a plug.

The body of the connecting element is on its external surface near the mouth of the feeding openings provided with numbers indicating the nominal internal diameters of nozzle openings and on the prolonged cone or on the external cylindrical part of the lower throughflow body with a number indicating the internal diameter of the cylindrical opening.

The new and improved effect of the arrangement according to this invention is in that the principle of its solution resides in a provision of a connecting element between the incubation tube and a fitting of a humidifying circuit or between a tube and the head piece of a bronchoscope. A cylindrical bore with a nominal internal diameter is provided in the body of said connecting element which diameter is equal to the nominal internal diameter of the intubation tube or of the tube of the bronchoscope. At least two openings are provided in the body of the connecting element, each of which contains a nozzle with a different nominal internal diameter of nozzle outlet openings, which nozzles terminate at the cylindrical bore so that the axis of nozzle openings intersect with the axis of the cylindrical bore at an angle of 10 to 30 angular degrees and the mouths of the nozzles do not extend into the cylindrical bore. The openings in the body of the connecting element form conical connections for an insufflation connector of a catheter with intermittent overpressure and for a catheter with constant overpressure with adjustable level. Similar connecting elements can be arranged to form a row having predetermined stepped nominal diameters of cylindrical bores and different nominal internal diameters of nozzle outlet openings and different nominal internal diameters of nozzle openings which are always at the approximately same ratio with the nominal internal diameter of the cylindrical bore of the connecting element.

BRIEF DESCRIPTION OF THE DRAWINGS

Exemplary embodiments of multinozzle generators for high frequency nozzle ventilation of lungs are shown in attached drawings, where FIG. 3 is a sectional elevation of a generator for application with a bronchoscope, FIG. 4 is a side view thereof.

DESCRIPTION OF PREFERRED EMBODIMENTS

Figure 1:
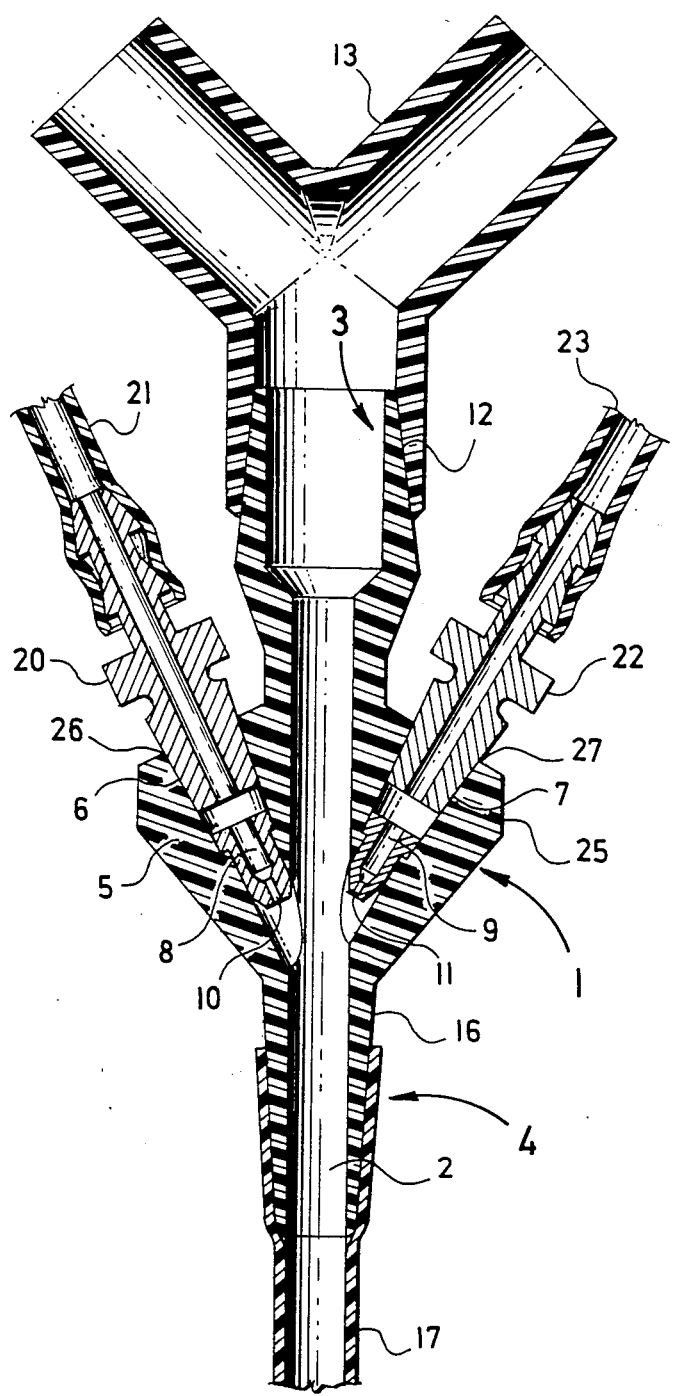
FIG. 1 is a sectional elevation of a generator for application with an intubation tube.
Figure 2:
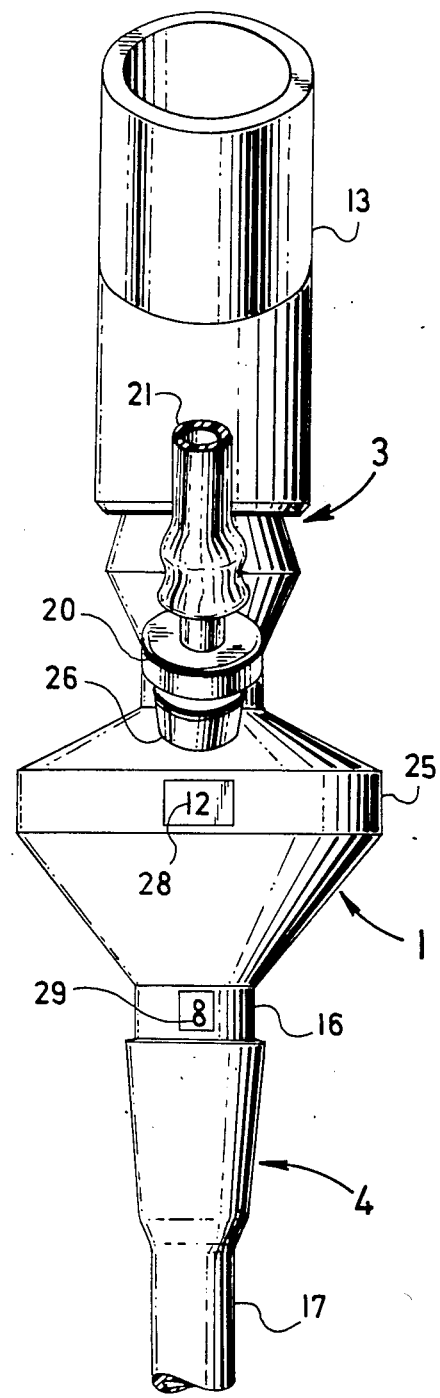
FIG. 2 is a side view thereof.
Figure 5:
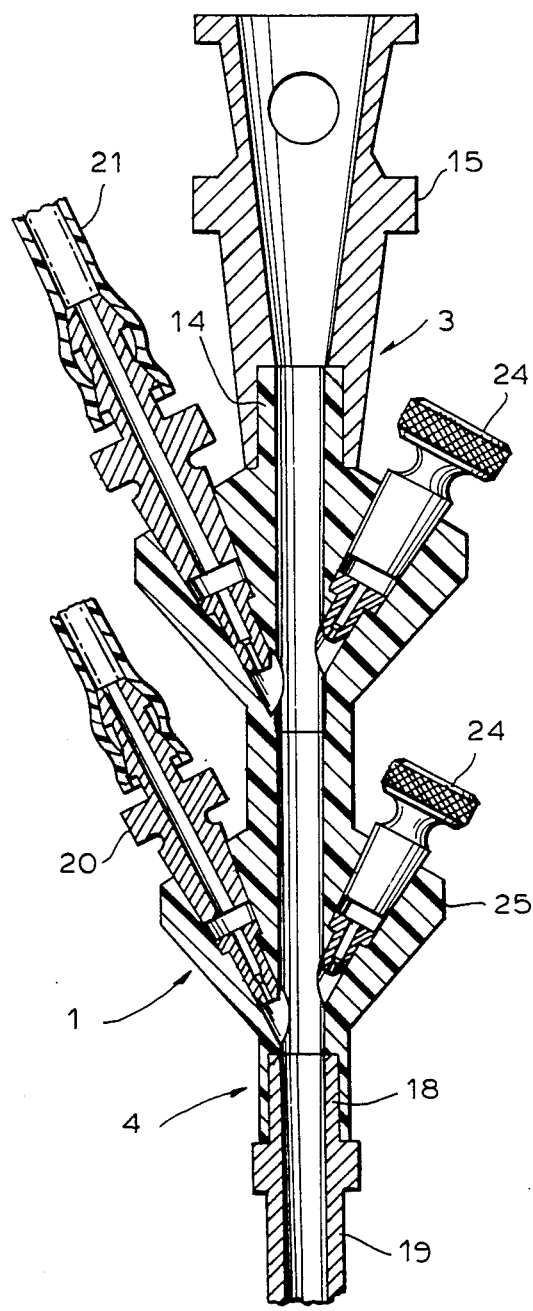
FIG. 5 is a view similar to FIGS. 1 and 3, showing an alternative embodiment of the invention.

With reference to FIGS. 1 and 2 the generator for high frequency nozzle ventilation of lungs comprises a connecting element generally designated with reference number 1 provided with a cylindrical bore 2 of a nominal internal diameter. The connecting element 1 is provided on one end with an upper throughflow connection 3 and on the other end with a lower throughflow connection 4. At least two feed conduits 6, 7 lead into the bore 2 and are provided with nozzles 8 and 9 and mounted in the body 5 of the connecting element 1. The nozzles 8 and 9 have corresponding nozzle openings 10 and 11 of different nominal diameter which terminate at the cylindrical bore 2. The axes of the nozzle bores 10, 11 intersect with the axis of the cylindrical bore 2 at an angle of 10 to 30 angular degrees. Similar connecting elements of the afore-described type can form a stepped row of such elements, determined by stepped nominal internal diameters of the cylindrical bore 2 and the different nominal internal diameters of nozzle bores 10, 11, so that for each connecting element 1 approximately the same ratio of nominal internal diameters of the cylindrical bore 2 is present.

The upper throughflow connection 3 forms an external conical surface 12 for connection to a fitting of a humidifying circuit 13 (FIG. 1) or an upper firm connection 14 for connection to a head 15 of a bronchoscope (FIG. 3). The lower throughflow connection 4 forms an elongated cone 16 for the intubation tube 17 (FIG. 1) or a lower firm connection 18 of a tube 19 of the bronchoscope (see FIGS. 3 and 4). The nominal internal diameter of the cylindrical bore 2 is equal to the nominal internal diameter of the intubation tube 17 (FIG. 1) of the tube 19 of the bronchoscope (FIG. 3).

The feeding conduits 6 and 7 form standard conical connections for an insufflation connector 20 of a catheter 21 with intermittent overpressure or for a connector 22 of a catheter 23 with constant overpressure (FIG. 1) or finally for a plug 24 (FIG. 3).

Indicia 28 indicate for an operator of the device the nominal internal diameter of nozzle bores 10 and 11 (for example the number 12 is shown in FIG. 1). These indicia are provided on the external surface 25 of the body 5 of the connecting element 1 close to the mouths 26 and 27 of openings 6 and 7 and on another place of the surface 25 of the body 5 indicia 29 are provided for indicating the nominal internal diameter of the cylindrical opening 2 (for example the number 8 is shown in FIG. 1).

MANNER OF OPERATION

The operation of the multinozzle generator will be explained in conjunction with exemplary embodiments shown in the drawings.

Operation of the multinozzle generator when connected to an intubation tube (FIG. 1).

The connecting element 1 forming the multinozzle generator is connected via the elongated cone 16 to the intubation tube 17, by the cone 12 to the fitting 13 of a humidifying circuit, by the insufflation connector 20 connected to the opening 6 or 7 to the catheter 21 with intermittent overpressure and by the connector 22 to the catheter 23 with constant overpressure.

The pressure in the catheter 21 with intermittent overpressure transforms the speed of gases in the nozzle bores 10 or 11 respectively. The outgoing stream is turbulent and sucks from the cylindrical bore 2 the humidified gas from the fitting 13 of the humidifying circuit. With increased distance from the nozzle opening 10 or 11, respectively, the specific weight of the sucked-off gas is increasing and the mean velocity in the widening stream is reduced. At the place where the turbulent cone of streaming gases touches the walls of the cylindrical bore 2, or the walls of the intubation tube 17, a dynamic closure of the air passages of the patient is accomplished and the overpressure determined by the kinetic energy of gases surpasses the throughflow resistance of air passages and the elastic resistance of the lungs of the patient so that gases are supplied to the lungs. In the course of the following time the volume of inhaled gases increases and the overpressure in the lungs increases due to elastic resistance of lungs. Due to the overpressure in the lungs the pressure gradient between the generator and the lungs is reduced and the throughflow to the lungs is reduced.

The maximum pressure of the generator is approximately proportional to the product of the overpressure in the catheter 21 with intermittent overpressure and to the square of the nominal internal diameter of the nozzle opening 10 or 11, respectively, and of the nominal internal diameter of the cylindrical bore 2. At least two nozzles 8 and 9 with different internal diameters for the nozzle outlet openings 10, 11 are arranged in the multinozzle generator; it is however possible to increase this number to four, each of which then has a different internal diameter for its nozzle outlet opening. The different internal diameters of nozzle outlet openings 10, 11 of the multinozzle generator enables selection of a different maximum overpressure of the generator even in case the insufflation overpressure is maintained and thus to adjust the generator to the instantaneous clinical condition of the patient.

For instance in case of a ventilation assistance, where the high frequency ventilation is superposed to the spontaneous activity of the patient, it is advantageous to select the ratio of the nominal internal diameter of the nozzle opening and of the nominal internal diameter of the cylindrical opening by a relatively low value, reducing thus the maximum overpressure of the generator and its internal resistance and the generator adjusts itself better to the spontaneous activity of the patient.

In case of a controlled high frequency nozzle ventilation of lungs where a relatively high throughflow resistance of the air passages is experienced, it is advantageous to select a nozzle with a higher nominal internal diameter of the nozzle opening, thus increasing the overpressure of the generator and the internal resistance of the generator, whereby an increased energetic drop between the generator and the alveolar space is achieved and simultaneously the decrease of the aspiration throughflow whereby the alveolar ventilation is increased.

Connection elements 1 forming a stepped row of such elements determined by stepped nominal internal diameters of cylindrical bores 2 form a stepped row of multinozzle generators in such a way, that for instance in case of a ventilation of a prematurely born child there is a ventilation similar to that of an adult. This similarity is determined by the same ratio of nominal internal diameters of nozzle openings of nominal internal diameters of cylindrical outlet openings. Thus it is possible to prevent any overpressure damages of lungs and simultaneously simplify the programming of high frequency nozzle ventilation.

In case an increase of the final expiration overpressure is needed, it is possible to connect to the sockets 6 or 7, respectively, where no insufflation connector 20 is present, to a connector 22 of a catheter 23 with constant overpressure. Thus a constant overpressure is secured in the intubation tube 17, the level of which can be adjusted by the value of a constant overpressure in the catheter 23 and the overpressure power of the generator is superposed on the constant overpressure power.

The arrangement of nozzles 8 and 9 in the body 5 of the connecting element 1 without extension of the mouths of the nozzles 8, 9 into the cylindrical bore 2 enables the introduction of a sucking-off catheter by way of the cylindrical bore 2 into the intubation tube 17 and its free movement during its introduction into the right or left bronchus in the course of ventilation. In case of the application of a sucking-off catheter, the throughflow cross section of the cylindrical bore 2 is relatively reduced whereby the maximum value of the generator overpressure and of the internal resistance of the generator is increased and the result is a reduction of theminute ventilation. The maintenance of ventilation requires an increase of the overpressure in the catheter 21 with intermittent overpressure.

Operation of the multinozzle generator when connected to a bronchoscope (FIG. 3).

The multinozzle generator forming the connecting element 1 is by the upper firm connection 14 connected to the head 15 of a bronchoscope and by the lower firm connection 18 to the tube 19 of the bronchoscope. By mounting the insufflation connector 20 in the receiving sockets 6 or 7 the catheter 21 with intermittent overpressure and, if required by mounting the connector 22, the catheter 23 with constant overpressure is connected.

The operation of the multinozzle generator connected to a bronchoscope is the same as the operation of a multinozzle generator connected with the intubation tube.

From the description of the exemplary embodiments of the multinozzle generator and of its operation, the following advantages are obvious: reduction of the danger of a damage of lungs due to overpressure, simplification of programming of the ventilation, simple extension of the ventilation by a single ventilator without limitation of size, weight and age class of the patients, sucking-off in the course of ventilation, simple generation of the final expiration overpressure.

Although a limited number of embodiments of the invention have been illustrated in the accompanying drawings and described in the foregoing specification, it is to be especially understood that various changes, such as in the relative dimensions of the parts, materials used, and the like, as well as the suggested manner of use of the apparatus of the invention, may be made therein without departing from the spirit and scope of the invention, as will now be apparent to those skilled in the art.

We claim:

1. An improved multinozzle generator for high frequency nozzle ventilation of lungs, the improvement comprising a connecting element comprising a body with a cylindrical bore therethrough having a nominal internal diameter and having first connection means at one end of said cylindrical bore adapted to be operatively mounted to a device used for treatment of lungs, such as a broncoscope, and second connection means at the opposite end of said cylindrical bore adapted to be mounted to a tube, such as an intubation tube, introduced into air passages of a patient, at least two feeding inlet openings provided in said body, nozzles with nozzle outlet openings of different internal diameter operatively mounted in said inlet openings and terminating at said cylindrical bore, the axes of the nozzle outlet openings intersecting with the axis of the cylindrical bore at an angle ranging from 10 to 30 angular degrees.

2. The improved multinozzle generator as set forth in claim 1, having a plurality of said connecting elements operatively connected to each other so as to form a stepped row of decreasing diameters in said connecting elements, each one of said stepped row of connecting elements comprising a body having a cylindrical bore extending therethrough of predetermined diameter smaller than the diameter of a bore of a preceding element, each of said first means being operably connectable to the second connection means of a preceding element such that, when said elements are connected together, said respective bores of said elements form said stepped row of decreasing diameters, and having, at least two feeding inlet openings provided in each body, nozzles with nozzle outlet openings of different internal diameter operatively mounted in said inlet opening of each body and terminating at said cylindrical bore, the axes of the nozzle outlet openings intersecting with the axis of each cylindrical bore at an angle ranging from 10 to 30 angular degrees, said internal diameters of the nozzle outlet openings and cylindrical bore diameter of each connecting element having substantially the same ratio.

3. The improved multinozzle generator as set forth in claim 1, wherein the first connection means has an external frusto-conical shape for connection to fittings of a humidifying circuit, the second connection means has an external frustoconical shape for connection with an intubation tube, the nominal internal diameter of the cylindrical bore being equal to the nominal internal diameter of the intubation tube.

4. The improved multinozzle generator as set forth in claim 1, further comprising a bronchoscope tube, wherein the first connection means has an external frusto-conical shape for connection of a head piece of a bronchoscope, the second connection means is firmly connected with said tube of the bronchoscope, the nominal internal diameter of the cylindrical bore is equal to the nominal internal diameter of the tube of the bronchoscope.

5. The improved multinozzle generator as set forth in claim 4, including an insufflation catheter connector adapted to communicate with intermittent overpressure connected to one of said feeding inlet openings.

6. The improved multinozzle generator as set forth in claim 4, including a catheter connector adapted to communicate with constant overpressure connected to one of said feeding inlet openings.

7. The improved multinozzle generator as set forth in claim 4, including a plug closing at least one of said feeding inlet openings.

8. The improved multinozzle generator as set forth in claim 1, wherein sid first connection means of said connecting element is adapted to connect with any one of a plurality of fittings which are designed as standard conical connections for auxiliary appliances.

9. The improved multinozzle generator as set forth in claim 1, wherein the body of the connecting element is provided on its external surface near each feeding inlet openings with numbers indicating the internal diameter of the respective nozzle outlet openings and at the lower part of said body a number indicating the nominal internal diameter of the cylindrical bore of the body of the connecting element.

* * * * *